US00PP17790P3

(12) United States Plant Patent
de Castro Filho

(10) Patent No.: US PP17,790 P3
(45) Date of Patent: Jun. 5, 2007

(54) ***ANANAS LUCIDUS* MILLER PLANT NAMED 'XANDA'**

(50) Latin Name: *Ananas lucidus*
Varietal Denomination: Xanda

(75) Inventor: Estevam Emygdio de Castro Filho, Fortaleza (BR)

(73) Assignee: Quinta Das Flores AgroExportadora Ltda., Fortaleza, CE (BR)

( * ) Notice: Subject to any disclaimer, the term of this patent is extended or adjusted under 35 U.S.C. 154(b) by 0 days.

(21) Appl. No.: 11/102,919

(22) Filed: Apr. 11, 2005

(65) Prior Publication Data

US 2006/0230483 P1 Oct. 12, 2006

(51) Int. Cl.
*A01H 5/00* (2006.01)

(52) U.S. Cl. ..... Plt./156
(58) Field of Classification Search ..... Plt./156, Plt./370
See application file for complete search history.

(56) References Cited

FOREIGN PATENT DOCUMENTS

EM 2005/1591 8/2005

OTHER PUBLICATIONS

Van Der Arend, R. "Openstaan voor elkaars ideeën resulteert in beste kwaliteit", *FLORAHOLLAND,* May 6, 2006, vol. 4, pp. 28–29. Article title translated is "Being Open–Minded to Each Others Ideas Result in the Best Quality".

*Primary Examiner*—Kent Bell
*Assistant Examiner*—June Hwu
(74) *Attorney, Agent, or Firm*—Foley & Lardner LLP

(57) ABSTRACT

A new and distinct cultivar of *Ananas lucidus* Miller plant named 'Xanda', characterized by having upper leaf surfaces which are brilliant red-orange in the middle, ranging from red, RHS 48B, at the base through red, RHS 43A, at mid leaf to red, RHS 46A, close to the tip, with dark brown, RHS 200A, borders, lightening towards the tip; a long which is colored green-yellow, RHS 1D; and peduncle coloration which starts with green-yellow, RHS 1D, from the middle onwards and turns into orange-red, RHS 35B, and ends with red, RHS 39A.

4 Drawing Sheets

1

Latin name of the genus and species of the plant claimed: The plant genus is *Ananas*. The plant species is *lucidus*.
Variety denomination: 'Xanda'.

FIELD OF THE INVENTION

The present invention comprises a new and distinct variety of *Ananas lucidus* Miller plant, which is hereinafter referred to by the name 'Xanda'. The new cultivar's market class is that of ornamental potted, landscape, foliage and flower cuttings plants.

The new *Ananas lucidus* Miller cultivar is a product of a planned breeding program conducted by the inventor, Estevam Emygdio de Castro Filho, in Paracuru, Brazil. The new *Ananas lucidus* Miller 'Xanda' originated from a naturally-occurring whole plant mutation in a batch of unnamed, unpatented *Ananas lucidus* Miller plants. The new *Ananas lucidus* Miller 'Xanda' was discovered and selected in 1997 by the inventor in a controlled environment in Paracuru, Brazil.

Asexual reproduction of the *Ananas lucidus* Miller 'Xanda' by side shoot cuttings was first performed in Paracuru, Brazil in 1997. The 'Xanda' plant exhibits a semi-perennial cycle. Eight generations of 'Xanda' have been grown since 1997, and the propagules are identical to the original 'Xanda'. Asexual reproduction of 'Xanda' has demonstrated that the combination of characteristics as herein disclosed for the new cultivar are firmly fixed and retained through successive generations of asexual reproduction. The new cultivar reproduces true to type.

2

DESCRIPTION OF PRIOR ART

The following characteristics were obtained by observing the prior art for plants of publicly known *Ananas lucidus* cultivars and plants of the instant cultivar 'Xanda', and are described below in Table 1:

TABLE 1

| Progress Stage | Characteristic | *Ananas lucidus* cultivars from prior art | *Ananas lucidus* 'Xanda' |
|---|---|---|---|
| A. The Plant (Vegetative progress stage) | Leaf Position: | Erect | Erect |
| | Plant Height: | 92 cm | 92 cm |
| | Plant Diameter: | 74 cm | 74 cm |
| B. The Leaf (Vegetative progress stage): | Leaf Length: | 82 cm | 81.5 cm |
| | Leaf width (in the middle of the leaf): | 36 mm | 38 mm |
| | Presence of thorns on the leaves: | Only the terminal | Only the terminal |
| C. Inflorescence (Stage of development with flowers in the middle of the inflorescence): | Length of the inflorescence: | 40 mm | 40 mm |
| | Diameter of the Inflorescence (Middle part): | 28.5 mm | 28 mm |
| | Length of the Peduncle: | 60 mm | 55 mm |
| | Diameter of the Peduncle (Middle part): | 10 mm | 11 mm |
| | Length of the Crown: | 20 mm | 20 mm |
| | Number of Bracts on the peduncle: | 9 | 10 |

TABLE 1-continued

| Progress Stage | Characteristic | *Ananas lucidus* cultivars from prior art | *Ananas lucidus* 'Xanda' |
|---|---|---|---|
| | Number of Bracts at the base of the fruit: | 3 | 3 |
| | Number of Berries on the fruit: | 69 | 80 |
| D. Presence of Offspring (Mature Fruit Stage): | Number of Offspring | High Quantity (more than 2) | High Quantity (more than 2) |
| | Number of Sapling-Offspring | High Quantity (more than 2) | High Quantity (more than 2) |
| | Number of Saplings at the base of the fruit | Medium Quantity (5 to 10) | Medium Quantity (5 to 10) |

SUMMARY OF THE INVENTION

The major characteristics of 'Xanda' include erectness as a plant, fruit less than 15 cm in height when at the adult stage, straight, dark reddish thornless leaves terminating in thorns, and a long, dark reddish stalk.

The following traits which have been repeatedly observed and are determined to be basic characteristics of 'Xanda', which in combination distinguish 'Xanda' from other cultivars of *Ananas lucidus* Miller of the same general type.

1. The leaf upper surfaces are brilliant red-orange in the middle, ranging from red, RHS 48B, at the base through red, RHS 43A, at mid leaf to red, RHS 46A, close to the tip, with dark brown, RHS 200A, borders, lightening towards the tip.
2. The 'Xanda' stalk is long and colored green-yellow, RHS 1D.
3. The peduncle starts with green-yellow, RHS 1D, color, from the middle onwards and turns into orange-red, RHS 35B, and ends with red, RHS 39A. Plants of the new cultivar of *Ananas lucidus* Miller 'Xanda' are distinguished from the unnamed, unpatented parent *Ananas lucidus* as having more brilliant red-orange upper leaf surfaces.

BRIEF DESCRIPTION OF THE DRAWINGS

The invention, together with the other objects, features, aspects and advantages thereof will be more clearly understood from the following in conjunction with the accompanying drawings.

Four sheets of drawings are provided. Sheet one contains FIG. 1. Sheet two contains FIG. 2. Sheet three contains FIGS. 3 and 4. Sheet 4 contains FIGS. 5 and 6.

BOTANICAL DESCRIPTION OF THE PLANT

Figure 1:
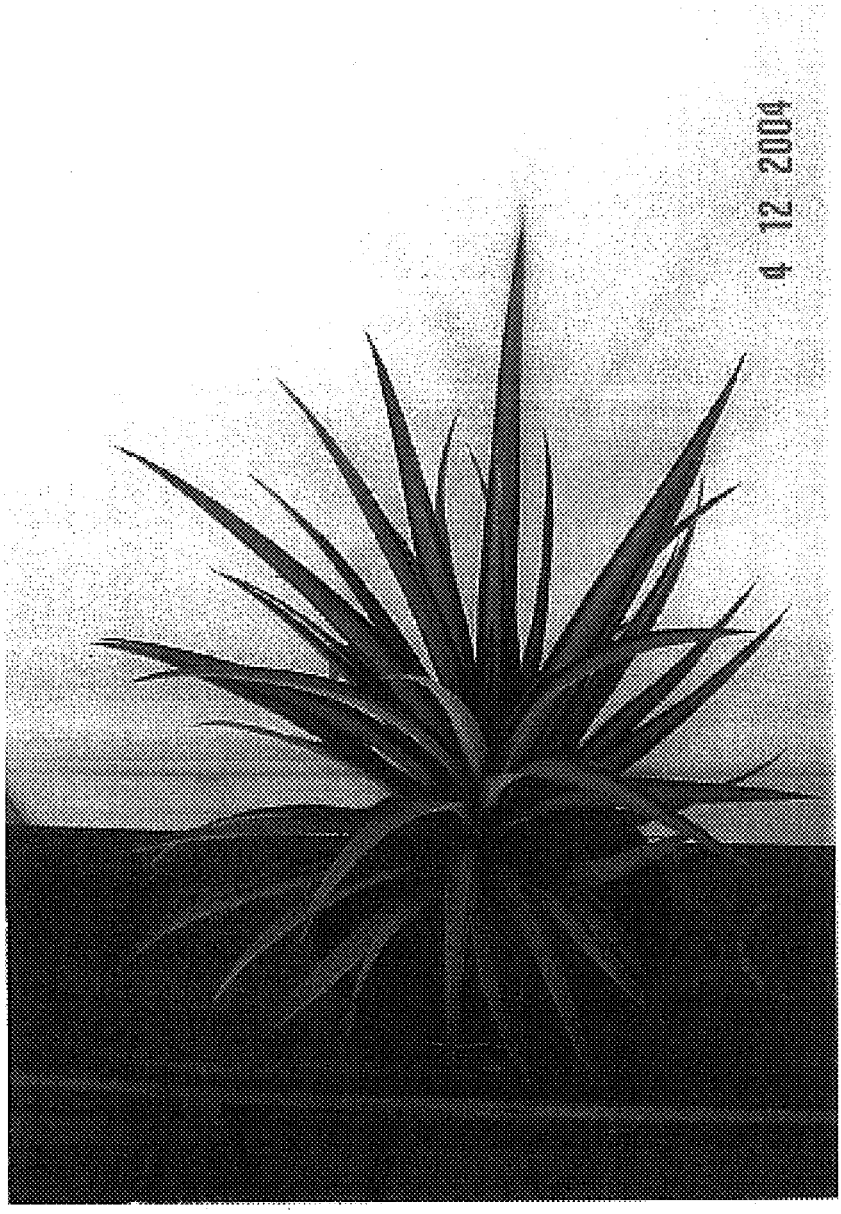
FIG. 1 is a color photograph of a front view of an *Ananas lucidus* Miller 'Xanda' plant which has not yet flowered.

FIG. 1 is a color photograph of a front view of an *Ananas lucidus* Miller 'Xanda' plant which has not yet flowered. The plant is ten months old. The distinctive leaf color is illustrated in FIG. 1. Leaf upper surfaces are brilliant red-orange in the middle, ranging from red, RHS 48B, at the base through red, RHS 43A, at midleaf to red, RHS 46A, close to the tip, with dark brown, RHS 200A, borders, lightening towards the tip. This brilliant red-orange coloration is in stark contrast to prior art *Ananas lucidus* Miller plants, which exhibit a dull rust-brown center leaf coloration. Leaf lower surfaces are grayed-green, RHS 197A, with dull red stripes, RHS 48C at the base, RHS 48A at midleaf, and RHS 52B toward the tip.

Figure 2:
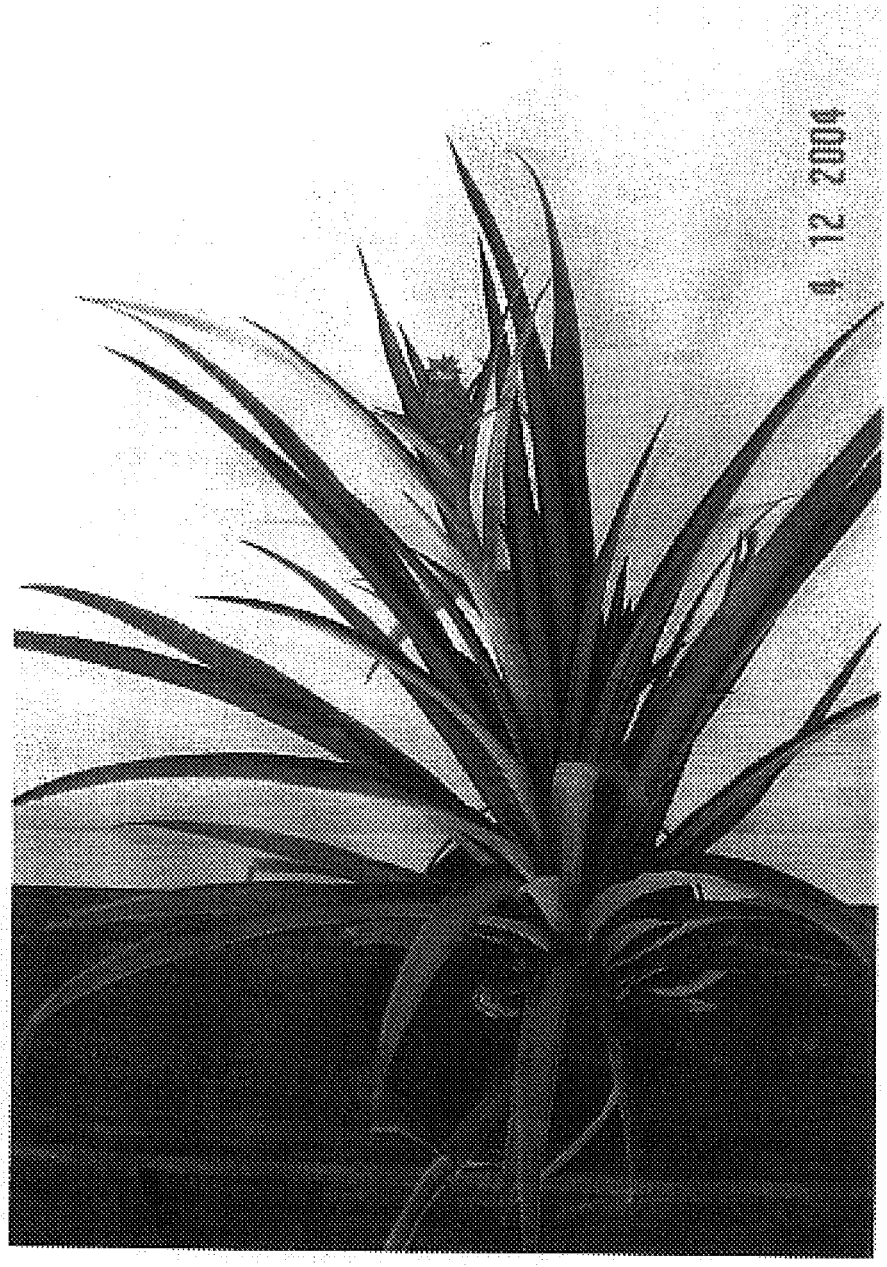
FIG. 2 is a color photograph of a top view of an *Ananas lucidus* Miller 'Xanda' plant which has flowered.

FIG. 2 is a color photograph of a top view of an *Ananas lucidus* Miller 'Xanda' plant which has flowered. The plant is ten months old, and was gassed with ethephon four months previously. One method to induce flowering in *Ananas lucidus* Miller 'Xanda' plants is to gas with ethephon. Upon flowering, the brilliant red-orange coloration of the leaves and peduncle increases in intensity, and darkens slightly. As the *Ananas lucidus* Miller 'Xanda' plants age, their coloration darkens.

Figure 3:
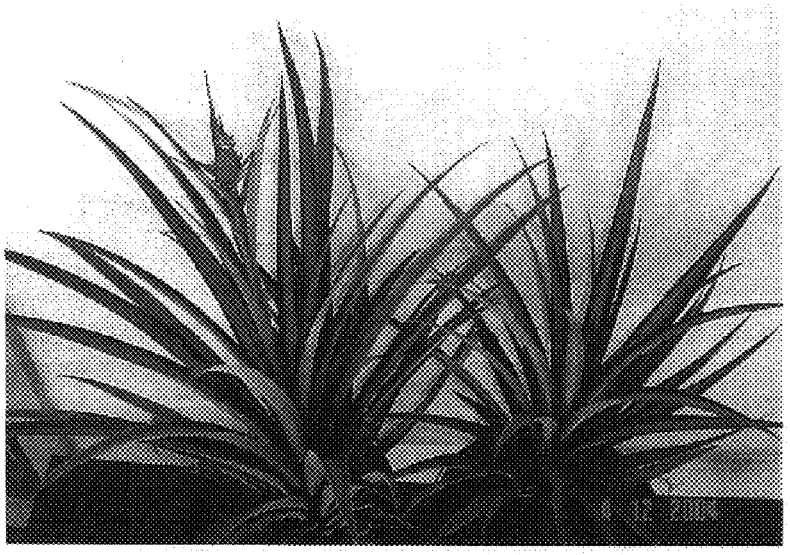
FIG. 3 is a color photograph of an *Ananas lucidus* Miller 'Xanda' plant which has flowered on the left, and an *Ananas lucidus* Miller 'Xanda' plant which has not yet flowered on the right.

FIG. 3 is a color photograph of an *Ananas lucidus* Miller 'Xanda' plant which has flowered on the left, and an *Ananas lucidus* Miller 'Xanda' plant which has not yet flowered on the right. The flowering plant is ten months old; the non-flowering plant is seven months old.

Figure 4:
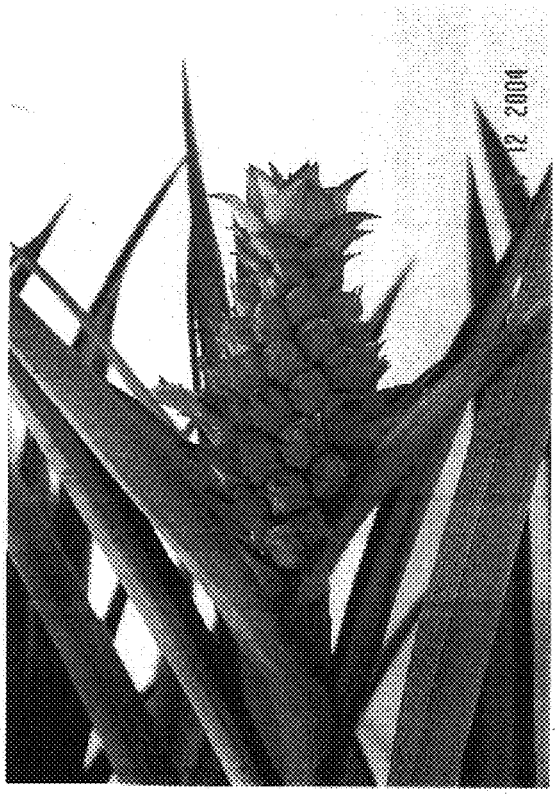
FIG. 4 is a color photograph of a close-up view of an *Ananas lucidus* Miller 'Xanda' fruit.

FIG. 4 is a color photograph of a close-up view of an *Ananas lucidus* Miller 'Xanda' fruit, which is colored red, RHS 48C RHS 49A. This specimen came from a 'Xanda' plant ten months old. One of the characteristics of the *Ananas lucidus* Miller 'Xanda' cultivar is the height of the fruit, which does not exceed 15 cm. The leaflets stemming off the peduncle exhibit a central stripe of brilliant orange-red color as do the other 'Xanda' leaves, typically being colored orange-red, RHS 34A.

Figure 5:
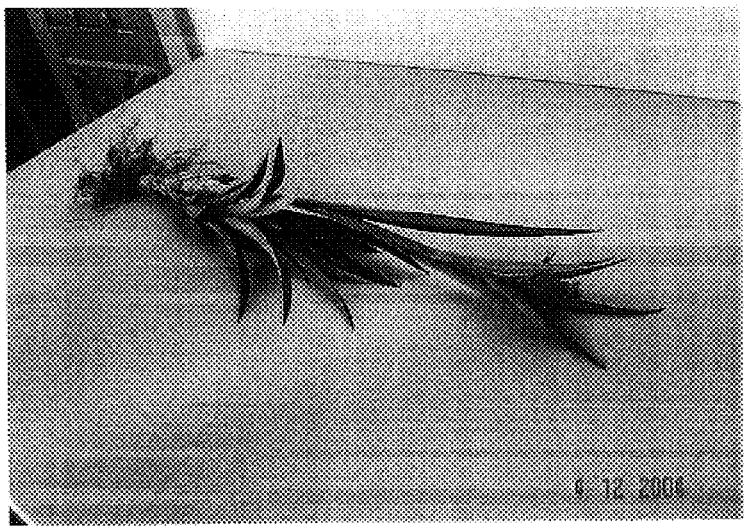
FIG. 5 is a color photograph of an *Ananas lucidus* Miller 'Xanda' showing the peduncle coloration and roots.

FIG. 5 is a color photograph of an *Ananas lucidus* Miller 'Xanda' showing the peduncle coloration and roots. The 'Xanda' stalk is long and colored green-yellow, RHS 1D. The peduncle is that portion of the plant which extends from the stalk to the fruit. The peduncle starts green-yellow, RHS 1D, turns orange-red, RHS 35B, from the middle onwards, and ends red, RHS 39A.

Figure 6:
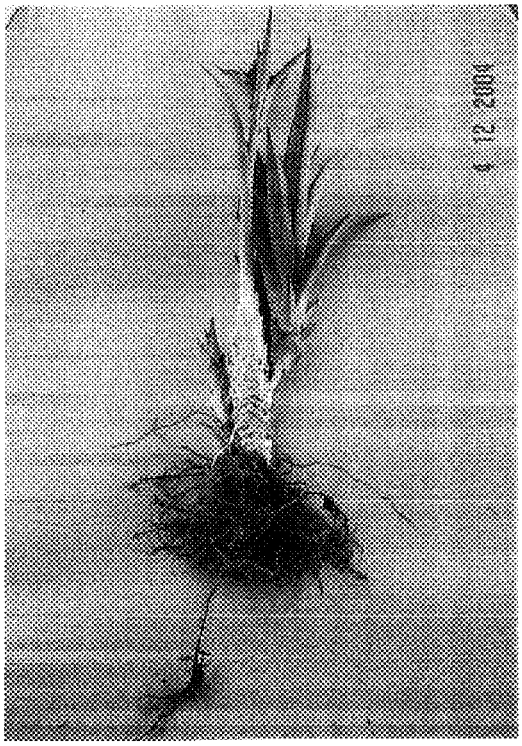
FIG. 6 is a color photograph of an *Ananas lucidus* Miller 'Xanda' showing the roots.

FIG. 6 is a color photograph of an *Ananas lucidus* Miller 'Xanda' showing the roots. The specimen depicted in FIG. 6 is ten months old.

The following Botanical Description describes plants of *Ananas lucidus* Miller 'Xanda' grown in San Pedro, Paracuru-Ceara, Brazil. The plants have not been observed under all possible environmental conditions. The phenotype may vary somewhat with variations in environment such as temperature, light intensity and/or fertilizer rate, without, however, any variance in genotype.

The *Ananas lucidus* Miller 'Xanda' plant comprises the following parts:

1. Stalk or main shaft, which the rest of the plant's organs are attached to or rest upon.
2. Root System, fascicled with eventual roots, divided in two categories: axillary (found in the axil of the basal leaves) and the underground (originated in the inferior part of the stalk, below the ground).

3. Lanceolate leaves with channel-shaped pipes, wrapped around the stalk and thornless, with the exception of the terminal thorn which is colored grey-orange, RHS 166C. The outer skin of the superior leaves presents a uniform, smooth, waxy layer, and has a reddish color in the central part of the leaf and a dark reddish color at the edges. The inferior outer skin is composed of grooves in the longitudinal direction, where stomas can also be found. The inferior outer skin is covered by peltates with scale-shaped trichomes, characterized by a white-silverish color and continuous fuzz.

Leaf upper surfaces are brilliant red-orange in the middle, ranging from red, RHS 48B, at the base through red, RHS 43A, at midleaf to red, RHS 46A, close to the tip, with dark brown, RHS 200A borders, lightening towards the tip. Leaf lower surfaces are greyed-green, RHS 197A, with dull red stripes, RHS 48C, at the base, RHS 48A, at midleaf, and RHS 52B toward the tip.

4. Peduncle: The part of the plant that develops like an extension of the stalk making a connection between the stalk and the fruit, sustaining the inflorescence and later on the green colored fruit at the base. The peduncle is covered by the presence of trichomes. The peduncle starts green-yellow, RHS 1D, turns orange-red, RHS 35B, from the middle onwards, and ends red, RHS 39A.

5. Sapling or seedlings that produce axillary buds and classified according with the position of the plant, in seedling (found in the connection of the peduncle with the base of the fruit), sapling-seedling (found in the connection of the peduncle with the base of the stalk), and sapling (found in the inferior part of the shaft, being airborne if it is above the ground and underground if below the ground).

6. The inflorescence originates from the apical meristem of the stalk, being a spike type, where the concrescent flowers are sessile (deprived of the peduncle) and are inserted along a shaft exposed in a spiral. The flowers are hermaphrodites and are located in the axial of a floral bract, about 12 mm in length and about 11 mm in width (52 days after floral induction with ethephon), dense, pulpous and deltoid-shaped. The top side of the bract has a green coloring, RHS 143C, at the base, with a red coloring, RHS 48D, at the edges, and on the bottom side of the bract has a green coloring, RHS 143C, at the base, with a red coloring, RHS 44A, at the edges. The flowers are trimerous, with three petals, about 11–15 mm in length and about 2–3 mm in width, linear-shaped, and colored white, RHS 155A, on the bottom side of the petal, and violet-blue, RHS N89D to purple-violet, RHS N81B, on the top side of the petal (52 days after floral induction with ethephon). The flowers also consist of three pulpous sepals, about 6 mm in length and about 7 mm in width, deltoid-shaped, and green coloring, RHS 143C, on the bottom side, and a red coloring, RHS 37C, at the edges, and the bottom of the sepal has a green coloring, RHS 143C, at the base, and a red coloring, RHS 55B, at the edges (52 days after floral induction with ethephon), with six stamens, about 7 mm in length, exposed in two floral verticals of three, and has a trilocular ovary, with one pistil, about 10 mm in length, a style and three stigmas.

7. The fruit is known as a frutescence, a composed fruit, a sorosis type, formed by the coalescence of the individual fruits (berries), berrylike fruits, inserted in a central shaft being-exposed in a spiral, composed by a carpology unit, with a cylindrical form, it has a low sappiness, weak aroma, the shin of the fruit originated from the union of the bracts and the sepals. The fruit is red RHS 48C–RHS 49A.

8. The crown is a continuation of the growth by the fruit producing new leaves giving as a product an erect crown elevating the fruit. The terminal crown (coma) is lanceolate-shaped, and averages about 1.7 cm in height, with leafy bracts, about 2.3 mm in length and about 10 mm in width, which are colored on the top side a yellow-green color, RHS 150D, at the base, and green, RHS 143D, at the edges. The bottom side of the leafy bracts are colored a yellow-green color, RHS 150D, at the base, and green, RHS 138C, at the edges (52 days after floral induction with ethephon). After 147 days after floral induction with ethephon, the shape of the crowns are still lanceolate-shaped, and average about 1.81 cm in height, with leafy bracts, about 127 mm in length and about 12 mm in width, and the coloring on the top-side is yellow-green, RHS 150D, at the base, and brown, RHS N200A, at the edges, with stripes of a red color, RHS 43C, at the base and red RHS 43D on the edges. The bottom side of the leafy bracts is yellow-green, RHS 150D, at the base, and grey-brown, RHS N199A, at the edges with stripes of a red RHS 36A to RHS 44D at the base, and red, RHS 37A to RHS 43C on the edges. The plant is moderately susceptible to fusariose, doesn't tolerate soaking, and is susceptive to wither because of the Mealybugs.

Growth Cycle: The *Ananas lucidus* Miller 'Xanda' grows erectly, is herbaceous and semi-perennial, and about 70–110 cm in height. The roots appear at the stem. The roots at the lower part of the stem penetrate the ground and the roots at the higher part surround the stem. The secondary roots develop themselves at the pericycle of the main root (adventical roots), after emerging from the stem. The stem develops itself from the semi-ellipsoidal pulp of the young plant used in the planting. As new leaves develop themselves in their apical meristem, the stem grows longer and thicker. The leaves originate as lateral projections from the apical region of the growth from the shaft of the stem, and develop in the direction of the apex. The inflorescence appears from the difference of the apical meristem. With the appearance of the inflorescence the rosette leaves gradually become distinguishable from the peduncle. Each eye represents an extreme of each individual flower, and develops into a berry-like fruit.

All color codes refer to "The Royal Horticultural Society London, 2001 Ed." Colors and leaf size may vary somewhat depending on horticultural practices such as light levels and fertilizer rates, among other things, without however, any variance in genotype.

I claim:

1. A new and distinct cultivar of *Ananas lucidus* Miller plant named 'Xanda', as herein described and illustrated.

* * * * *